(12) United States Patent
Beckman

(10) Patent No.: US 10,183,088 B2
(45) Date of Patent: Jan. 22, 2019

(54) SELF-CLEANING SURFACES

(71) Applicant: Christopher V. Beckman, San Diego, CA (US)

(72) Inventor: Christopher V. Beckman, San Diego, CA (US)

( * ) Notice: Subject to any disclaimer, the term of this patent is extended or adjusted under 35 U.S.C. 154(b) by 96 days.

(21) Appl. No.: 15/044,064

(22) Filed: Feb. 15, 2016

(65) Prior Publication Data
US 2016/0158396 A1    Jun. 9, 2016

Related U.S. Application Data

(63) Continuation-in-part of application No. 13/815,972, filed on Mar. 18, 2013, now Pat. No. 9,285,127, and a continuation-in-part of application No. 13/745,833, filed on Jan. 20, 2013, now Pat. No. 9,259,347.

(51) Int. Cl.
| | |
|---|---|
| *A61L 2/18* | (2006.01) |
| *F24D 17/00* | (2006.01) |
| *F24D 19/10* | (2006.01) |
| *E03B 1/04* | (2006.01) |
| *E03C 1/046* | (2006.01) |
| *A47K 5/12* | (2006.01) |
| *E03C 1/00* | (2006.01) |

(52) U.S. Cl.
CPC .............. *A61L 2/18* (2013.01); *E03B 1/048* (2013.01); *E03C 1/046* (2013.01); *F24D 17/0078* (2013.01); *F24D 17/0094* (2013.01); *F24D 19/1051* (2013.01); *A47K 2005/1218* (2013.01); *E03C 2001/005* (2013.01); *Y10T 137/6497* (2015.04)

(58) Field of Classification Search
CPC ......... A61L 2/18; E03C 1/046; E03C 1/0465; A47K 2005/1218; A47K 5/12; A47K 5/1204; A47K 5/1208; A47K 5/1211; A47K 5/1215; A47K 5/1218; B08B 9/032; B08B 3/00; E05B 1/0069
USPC ................... 137/15.05, 15.06, 237, 238, 240
See application file for complete search history.

(56) References Cited

U.S. PATENT DOCUMENTS

| | | | | |
|---|---|---|---|---|
| 4,832,942 | A * | 5/1989 | Crace | A61L 2/18 15/244.3 |
| 5,271,892 | A * | 12/1993 | Hanson | A61L 2/26 206/366 |
| 7,322,364 | B2 * | 1/2008 | Hurwitz | A01K 13/002 132/116 |
| 9,457,383 | B1 * | 10/2016 | Skerven | B08B 3/04 |
| 2010/0299828 | A1 * | 12/2010 | Shapiro | A47K 7/04 4/622 |

FOREIGN PATENT DOCUMENTS

DE    102009036339 B3 *  11/2010  .......... E05B 1/0069

OTHER PUBLICATIONS

Machine Translation for DE102009036339B3.*

* cited by examiner

*Primary Examiner* — Ian Paquette

(57) ABSTRACT

New forms of self-sterilizing and antiseptic surfaces are provided. In some embodiments, a handled surface or GUI comprises internal hardware performing a heavy rinse of the handled surface triggered by an end-of-use function. In other embodiments, pressure on a handled surface instead causes the surface to uniformly exude water and other antiseptic compositions from a refillable source.

15 Claims, 12 Drawing Sheets

SELF-CLEANING SURFACES

RELATED APPLICATION DATA

This application is a continuation-in-part of co-pending U.S. patent application Ser. No. 13/815,972, filed Mar. 8, 2013, the entire contents of which are hereby incorporated by reference in their entirety into the present application. This application is also a continuation-in-part of co-pending U.S. patent application Ser. No. 13/745,833, filed Jan. 20, 2013. This application claims the benefit of and claims priority to U.S. application Ser. No. 13/815,972, filed Mar. 8, 2013, and to U.S. application Ser. No. 13/745,833, filed Jan. 20, 2013.

FIELD OF THE INVENTION

The present invention relates to the field of fluid circulation technologies and antiseptic surfaces.

BACKGROUND

Indoor plumbing including metal pipes dates at least to ancient Rome. The Romans also implemented hot water heating systems, called hypocausts, which were used extensively in large communal baths. See, e.g., Nova Online, *Secrets of Lost Empires, Roman Bath, A Day at the Baths*, Part 6 (Caldarium) November 2000, available at http://www.pbs.org/wgbh/nova/lostempires/roman/day.html, accessed Mar. 17, 2013.

Modern plumbing systems implement many of the same techniques pioneered in Ancient Rome. As in Ancient Rome, hot water "burners" heat a container of water from below to elevate its temperature in buildings in the United States. Modern systems also use pipes to deliver water, with some refinements in materials and workmanship to improve their performance. Metal pipes, such as copper or brass, are still in use, but effective advanced materials have also been developed, such as cross-linked polyethylene ("PEX"). In the plumbing industry, copper pipes are still heralded as having many advantages over PEX, including greater durability (especially in outdoor environments) and resistance to contamination.

In homes with longer distances between hot water burners (and their associated hot water storage tanks) and served fixtures, the connecting pipes have enough length to create a substantial hot water service lag. After opening a hot water tap, hot water in the associated pipe has cooled in the wall over its entire length outside of the tank, and a user must wait until new hot water from the tank reaches the fixture. To combat this lag, hot water recirculation systems have been developed. In their simplest form, hot water recirculation systems may create a short bridge between the hot and cold services (typically, at the fixture in the circuit farthest away from the tank) to continuously supply new hot water to the points of service. A pump may be used, or, if the pipes are arranged properly (hot water service pipe at a lower level) the system may move water through the circuit continuously as a heat siphon. More complex systems for hot water recirculation involve additional pipes run out to fixtures, to complete such "on demand" hot water availability. Another form of lag-reduction technology is known as a "Home Run" or "manifold" system, where much smaller gauge pipes are run out to each fixture, individually, to reduce the amount of water to clear when a hot water tap is opened, and, therefore, the amount of hot water lag in using one fixture. However, home run systems may, ironically, create lag in some instances due to their separated structure, such as when multiple fixtures are in use on or about the same time. Nonetheless, all of these systems create substantial convenience for a user.

Antiseptic soaps have also been used in bathrooms, among many other rooms and uses, for quite some time. In general, hand washing, particularly before consuming or preparing food, is highly recommended by the medical community as among the best ways to fight the risk of several illnesses, such as the flu.

It should be understood that the disclosures in this application related to the background of the invention, in, but not limited to this section titled "Background," do not necessarily set forth prior art or other known aspects exclusively, and may instead include art that was invented concurrently or after the present invention and conception, and details of the inventor's own discoveries and work results.

SUMMARY OF THE INVENTION

New forms of self-sterilizing and antiseptic surfaces are provided. In some embodiments, a handled surface or GUI comprises internal hardware performing a heavy rinse of the handled surface triggered by an end-of-use function. In other embodiments, pressure on a handled surface instead causes the surface to uniformly exude water and other antiseptic compositions from a refillable source.

A specialized plumbing hardware system that performs new energy- and water-saving, restorative tasks upon the completion and initiation of use is also provided. In some aspects of the invention, energy saving hot water recapturing techniques are provided. For example, upon completing use of a hot water service outlet, a control system retracts hot water into an insulated hot water heating tank, rather than leaving it in external hot water pipes. In some aspects, the system pushes hot water through a return channel with trailing cold water, and halts such pushing after it senses the cold water arrive before the insulated tank, behind the returned hot water. In other aspects, the system may avoid delivery of requested water through the hot water service outlet unless and until hot water has arrived at that outlet, through the same bypass circuit described above. In still other aspects, a user-selectable auxiliary rapid hot water delivery device is provided, such as a local tank or flash copper coil heater near and/or partially in the fixture, or in a specialized pipe, to reduce lag caused by the energy- and water-saving aspects discussed above, and a user may select additional energy and water-saving options and settings, including, but not limited to, a "Final Rinse" option that may be timed to the user's choosing and/or habits.

In other aspects, a user's completion of use of a plumbing and related fixtures triggers an ending rinse of handled parts of those fixtures and, optionally, a soap or antiseptic spray or sweat about such parts. The same technology may be applied to other handles and fixtures, for example, about contact surfaces on a bathroom door or elevator buttons.

Where any term is set forth in a sentence, clause or statement ("statement"), each possible meaning, significance and/or sense of any term used in this application should be read as if separately, conjunctively and/or alternatively set forth in additional statements, as necessary to exhaust the possible meanings of each such term and each such statement.

It should also be understood that, for convenience and readability, this application may set forth particular pronouns and other linguistic qualifiers of various specific gender and number, but, where this occurs, all other logically possible gender and number alternatives should also be read in as both conjunctive and alternative statements, as if equally, separately set forth therein.

DETAILED DESCRIPTION OF THE INVENTION

Figure 1:
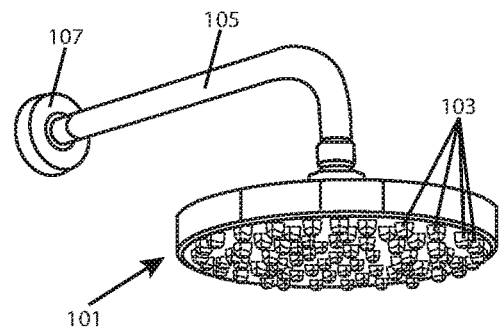
FIG. 1 is a perspective view of an exemplary fixture—namely, a shower head—capable of delivering, at least in part, hot water to a user for bathing.

FIG. 1 is a perspective view of an exemplary fixture 101—namely, a shower head—capable of delivering, at least in part, hot water to a user for bathing. As with many existing shower heads, shower head 101 comprises a plurality of jets capable of releasing water when adequately pressurized with water, such as those examples given as 103. A water supply pipe 105 is connected, and able to deliver such water pressure, to shower head 101, and through jets 103, overhead a user, providing her or him with a waterfall for bathing. Pipe 105 is shown entering a wall through a mounted and/or decorative bracket 107.

Figure 2:
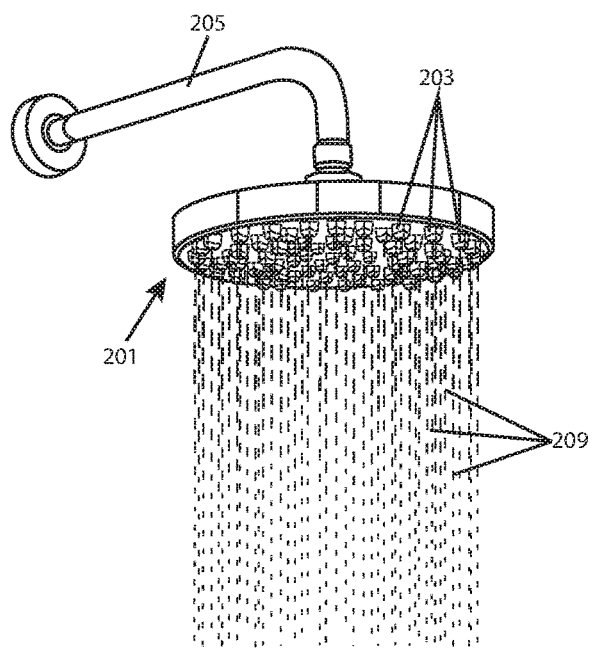
FIG. 2 is a perspective view of the same exemplary fixture as that discussed with reference to FIG. 1, shown deploying a shower of water.

FIG. 2 is a perspective view of the same exemplary fixture (now 201) as that discussed with reference to FIG. 1, shown deploying a shower of water for a user. Each water jet (such as those examples now shown as 203) now releases a stream or series of droplets of water, such as those examples shown as 209, which are then pulled downward and/or away from jets with gravity and/or the force of water pressure, as guided by the hollow inner contours of the jets. Again, the water pressure—now shown being supplied—emanates from the attached pipe, now 205.

Figure 3:
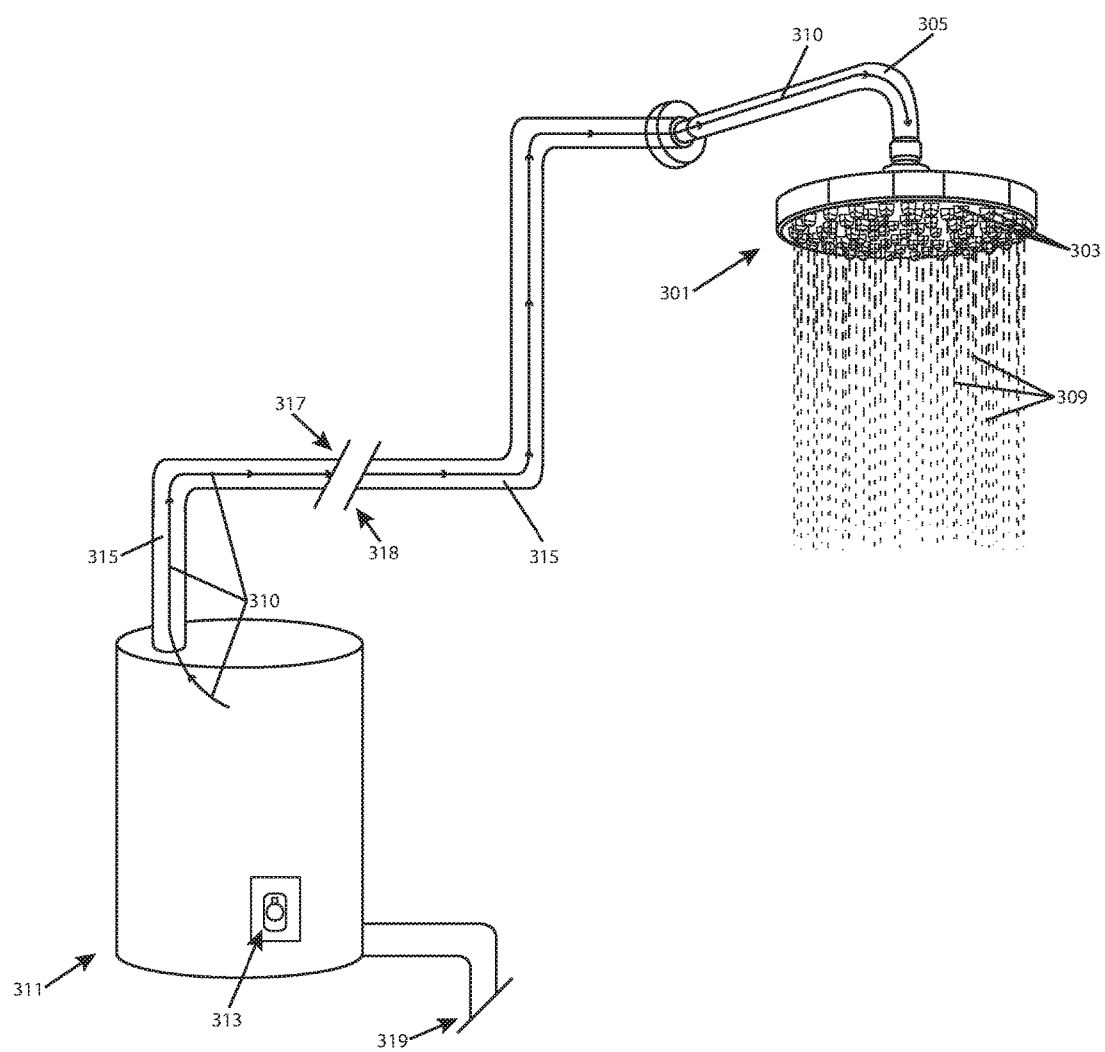
FIG. 3 is a perspective view of the same exemplary fixture as that discussed with reference to FIGS. 1 and 2, in connection with an exemplary hot water tank and delivery system.

FIG. 3 is a perspective view of the same exemplary fixture (now 301) as that discussed with reference to FIGS. 1 and 2, in connection with an exemplary hot water tank 311 and delivery system 300. Although not depicted, system 300 may comprise a power supply and control system, such as that discussed with reference to FIG. 11, below, for carrying out water heating, with a comprised settable thermostat 313, and hot water delivery through a hot water delivery pipe 315. For convenience, the entire length of delivery pipe 315, and all of its turns, are not depicted in FIG. 3 and, instead, an elision is made at point 317 (on the left hand side, from the perspective of the figure) and point 318 (on the right-hand side). Another elision is shown at point 319, to avoid unnecessary depiction of the entire water supply pipe 321, supplying water to tank 311. Upon receiving tap water from supply pipe 321, tank 311 may begin to heat that water, if thermostat 313 indicates that its internal water temperature is too low, according to its set level, using, for example, a burner, flash heating element, or both (not pictured).

Fixture 301 is, as in FIG. 2, shown supplying streams or droplet series, now shown as examples 309, after a hot water service knob (or other control) has been turned on by a user. When that occurs, a pump or other water pressure created in the system 300, or outside the system, causes hot water to flow from tank 311, through pipes 315 and 305, and out of the shower head jets, such as those examples now shown as 303. This water flow is shown by flow arrow 310.

Figure 4:
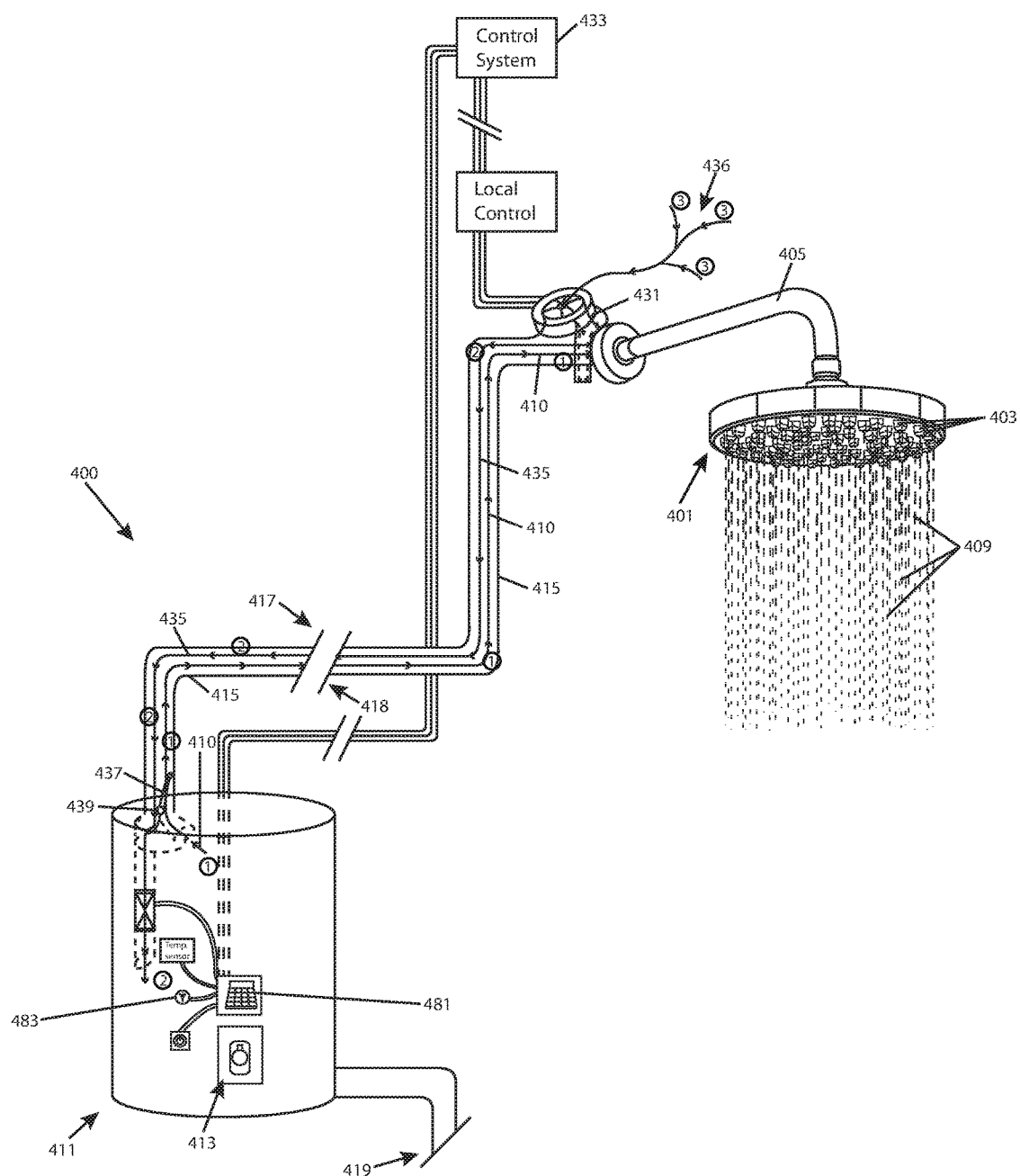
FIG. 4 is a perspective view of the same exemplary fixture as that discussed with reference to FIGS. 1-3, in connection with an exemplary hot water tank and delivery system implementing some waste heat reduction and water recapturing aspects of the present invention.

FIG. 4 is a perspective view of the same exemplary fixture as that discussed with reference to FIGS. 1-3, (now 401) in connection with a new exemplary hot water tank 411 and delivery system 400 implementing some waste heat reduction and water recapturing aspects of the present invention. For convenience, the latter two digits of each numbered aspect in FIG. 4 are the same as those of similar aspects set forth above, in reference to FIG. 3. For example, a hot water delivery pipe is set forth as 415. However, unlike hot water delivery pipe 315, from FIG. 3, hot water delivery pipe 415 includes a recapture-permitting valve 431, which variably permits air or another gas (e.g., argon or another noble gas, to prevent corrosion) to enter, as shown by flow arrow 436. To control the timing and effect of such variably-permitted entry, system 400 may comprise a control system 433, which may be such as, but not limited to, the hardware and/or software control system set forth below, with reference to FIG. 12.

For example, as mentioned above with reference to FIG. 3, as a user showers using hot water, that hot water may flow from tank 411 into pipe 315, and out of the shower head 401, as shown by water flow arrow 410, also shown as flow sequence (1)—the first of two flow directions. Upon finishing a shower using shower head 401, a user may shut off the hot water, using a control knob or GUI (not pictured) for actuating the control system 433 and/or hot water delivery from tank 411. Whereas in most home plumbing systems, hot water would then remain in the hot water delivery pipe, the control system 403 of system 400 may, instead, actuate valve 431, and/or a pump or other valve or stop (not pictured) to cause/permit unused hot water in pipe 415 to return to tank 411, as shown by flow arrow 435, also shown as flow sequence (2), and air to enter pipe 415, as shown in flow sequence (3), to fill the resulting vacuum. As the hot water returns to tank 411, a one-way valve 437 may prevent water flow 435 from passing into an open channel, from which water flow 410 emanated. During outflow, in flow sequence (1), flow 410 was able to pass through that channel because one-way valve 437 was pushed by that flow into another orientation, rotating on an axis/joint 439. But as flow 435 returns to tank 411, it is forced away from the open exit channel by valve 437 and, instead, may enter a filtration, purification and/or conditioning element (which may, in some embodiments, also heat returning water flow 410) before permitting it to enter tank 411. The control system may, in some embodiments, close valve 431, and/or other valves or halt pumping at or closer to tank 411, to prevent new hot water from entering pipe 415 unless and until it is summoned by a user and/or the control system. The control system may also sense when all available hot (or, at least, elevated temperature from the temperature of incoming supply pipe 421) water has returned to tank 411, and seal the inlet for flow 435. In some embodiments, the tank 411 may begin to supply positive pressure, with a completely sealed outflow at the tank, for example, using, in part an actuable valve covering the entire outflow connection to pipe 415.

In a subsequent sequence step (not pictured), the control system and/or user may again command hot water delivery at shower head 401, using the control system and/or hot water tap control—for example, by using a local control GUI, accessible to the user, or with which the user may enter settings causing the system to make such a command (e.g., daily routine information or behavioral detection by the control system). At that point, preferably, the control system opens (if closed) valve 431's upward opening port (within the wall) to pipe 415 and, preferably, closes another opening of pipe 415 that faces the shower head 401, and begins to send new hot water into pipe 415. As this occurs, the gas held in pipe 415 empties into the wall or, in some embodiments, the room comprising the shower head 401. In any embodiment, however, when hot water arrives at valve 431, valve 431 shuts the opening of pipe 415 in the wall and opens the opening facing the shower head 401. In some embodiments, the control system may sense water arrival, and actuate valves to carry out aspects of the invention. But, in other embodiments, a medium-specific reacting valve(s) may obviate the need for the control system to activate such valve(s). To absorb axial impact from rapidly rushing water, an expansion joint and/or axial bellows may be added to a length of pipe 415, or in communication with pipe 415.

System 400 may comprise a user-actuable user interface, such as GUI 481, connected to, powered by and capable of communicating with, the control system, and which may comprise, as pictured, an alphanumeric keypad and/or LCD display, or may have any other hardware known in the art for creating a GUI. In addition, control system 433 may be wirelessly connected with a network and other network aspects capable of delivering a GUI to a user, such as a smartphone or PDA, via wireless antenna 483.

Figure 5:
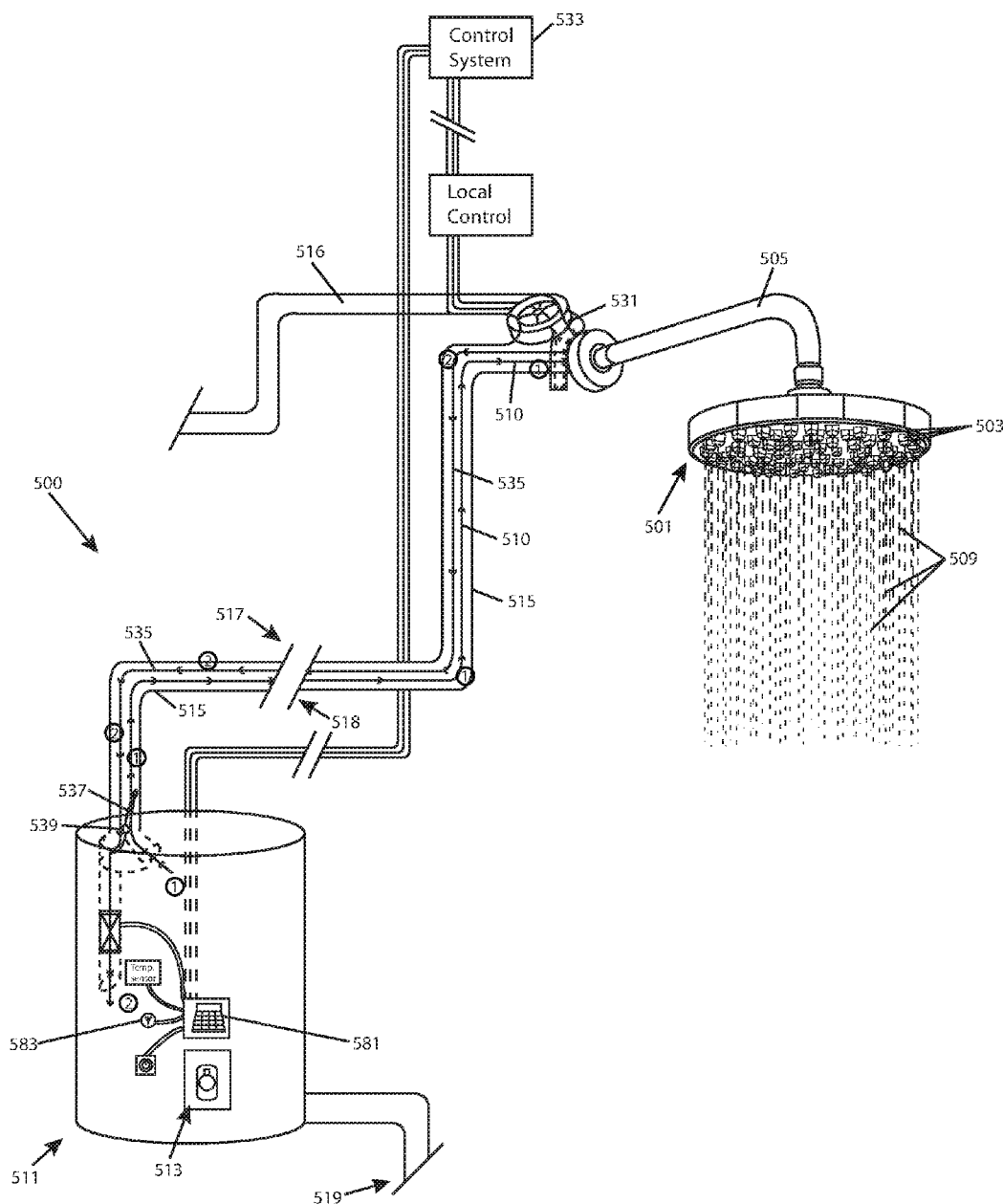
FIG. 5 is a perspective view of the same exemplary fixture as that discussed with reference to FIGS. 1-3, in connection with another embodiment of an exemplary hot water tank and delivery system, implementing additional waste heat and water recapturing aspects of the present invention.

FIG. 5 is a perspective view of the same exemplary fixture as that discussed with reference to FIGS. 1-3 (now 501), in connection with another embodiment of an exemplary hot water tank 511 and delivery system 500, implementing additional waste heat and water recapturing aspects of the present invention. System 500 is similar to system 400 and, as with FIG. 4 with respect to FIG. 3, in FIG. 5, for convenience, the latter two digits of each numbered aspect in FIG. 5 are the same as those of similar aspects set forth above, in reference to FIG. 4. As with FIG. 4, system 500 may comprise a control system 533, which, as in FIG. 4, orchestrates the sensing and control of particular water/fluid flows through a hot water delivery pipe 515. However, rather than voiding the hot water delivery pipe 515 of water, and filling it with air, system 500 instead may use a cold water service pipe 516 to push and/or replace hot water that is taken from pipe 515 into tank 511. In sufficiently hot environments, or in other circumstances where the temperature in the walls of the building or pipes exceeds the temperature of the water supply for tank 511, additional water, replacing the hot water returned to tank 511 may, itself, become sufficiently elevated that the system 500 derives an energy and/or home cooling benefit from retracting even at least some of that water into tank 511. The amount of elevation and water to so take in for eased heating, within tank 511, may be optimized based on the energy cost (if any) of so permitting that additional water flow. In colder environments, hot water may be pumped into the hot water supply pipe 515 and, in some embodiments, into a cold water supply pipe, to aid in heating the home. However, in such circumstances, an improved form of pipe is preferred, which will be set forth with reference to FIG. 6, below.

Figure 6:
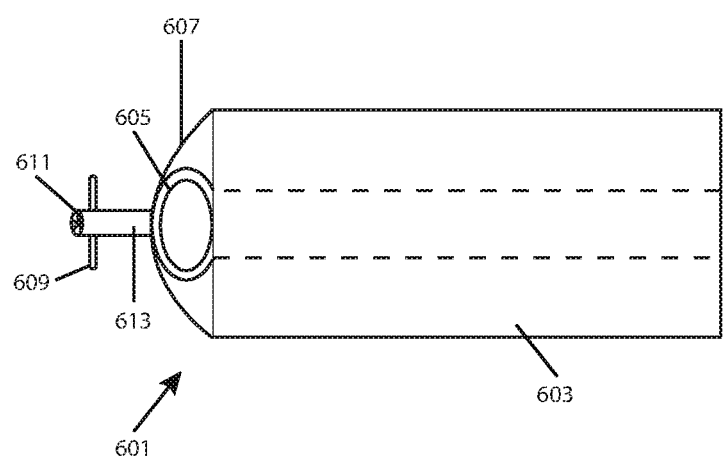
FIG. 6 is a side view of a section of specialized, heat-capturing plumbing pipe, as may be used to implement aspects of the present invention.

FIG. 6 is a side view of a section of specialized, heat-capturing plumbing pipe 601, as may be used to implement aspects of the present invention. A side 603 (of pipe 601) facing the viewer (the direction of the positive z axis) and on a plane running parallel with an inner pipe section 605, is substantially flat or otherwise shaped and/or designed to accommodate, abut, and/or control the orientation of pipe 601 relative to, an inner side of a wall in which it is installed. Another side, 607, opposite to side 603, comprises a heat-insulating and/or -reflecting material, that, preferably so insulates and reflects heat in the direction toward side 603, is also provided. A wall anchor 609 may be connected, periodically, to side 607, or another aspect of pipe 601, and may control the orientation and rotation of pipe 601 relative to the surrounding building walls. An optional screw-actuated or other control 611 of the anchor 609's stem 613 may connect with a ratcheting mechanism and/or translational gearing (not pictured) that may cause inner pipe section 605, pipe 601 and/or insulating/reflecting wall 605, to rotate relative to the wall and/or one another, and change the angle of reflected and/or insulated heat. Control 611 may be user- or, as with other actuable aspects of the invention, system-actuable.

For example, in hot locations and times, a user and/or the system may rotate the heat-capturing, insulating and/or reflecting wall, or another such layer, wherever situated on or about the pipe 601, to cause it to face outward, away from the building. In cold locations and times, a user and/or the system may reverse that rotation, until the heat-capturing, insulating and/or reflecting wall, or another such layer, faces inward, retaining building heat.

In some embodiments, stem 613 and control 611 may be variably-extendable, to create a variably tight fit and proper orientation of pipe 601 for various applications (e.g., wall widths).

Figure 7:
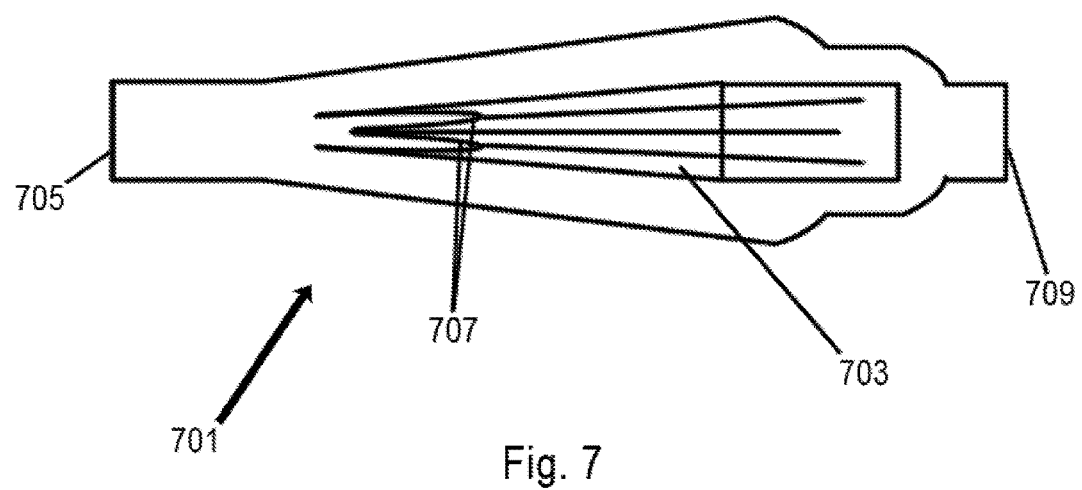
FIG. 7 is a side view of an exemplary section of new form of hot water delivery pipe 701 that provides flash heating of cold water in a hot water pipe just prior to delivery, reducing wasteful hot water cooling, in accordance with aspects of the present invention.

FIG. 7 is a side view of an exemplary section of new form of hot water delivery pipe 701 that provides flash heating of cold water in a hot water pipe just prior to delivery, reducing wasteful hot water cooling, in accordance with aspects of the present invention. Unlike with other flash and point-of-use heating devices, pipe 701 has a low profile, and may be used in place of a length of pipe that is already required to bridge the distance from a water heater and a fixture serviced by hot water from that tank. A heating element 703, which is preferably baffled, ciliated, folded or otherwise surface area-enhanced, heats water as it passes from the pipe section inlet 705, which may be connected to ordinary water supply pipe of substantially the gauge of the inlet channels water toward the leading edge of element 703 as it flows toward a serviced fixture, to the right. Preferably, element 703 is semi-porous and/or contains stream-lined inlet scoops 707, to increase surface area further, for heat exchange. Element 703 may be connected to, powered and controlled by, a control system, such as the control system set forth with reference to FIG. 12, below. Alternatively, element 703 may be powered by a more local power source, such as a local electrical service, to decrease unnecessary wiring resistance, through wires (not pictured) or other transmission. Element 703 may comprise any flash heating elements known in the art, including, but not limited to, copper heating coils, to heat water as it passes.

Preferably, heating pipe section 701 includes an increased width insofar as heating element 703 occupies a part of its inner diameter, to reduce physical resistance while maintaining good contact between the heating element 703 and water flowing through and around it, as that water progresses from inlet 705 to the fixture, through an outlet 709.

Figure 8:
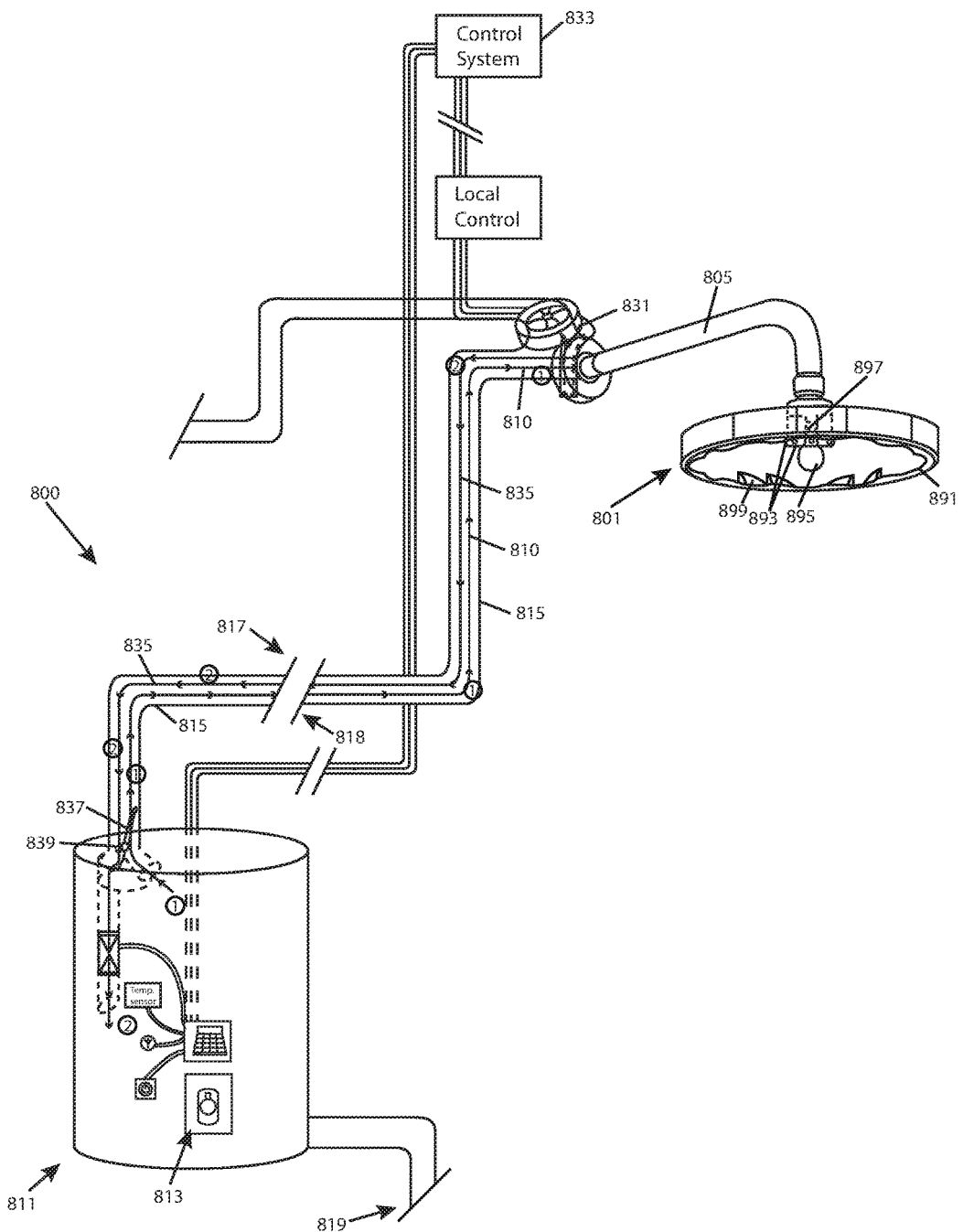
FIG. 8 is a partially cutaway perspective view of a specialized, exemplary shower head and hot water tank and delivery system, implementing constant-on hot water aspects to reduce or eliminate drawbacks of a system such as that set forth with reference to FIGS. 3-5 and 7, above, in accordance with additional aspects of the invention.

FIG. 8 is a partially cutaway perspective view of a specialized, exemplary shower head 801 and hot water tank and delivery system 800, implementing constant-on hot water aspects to reduce or eliminate drawbacks of a system such as that set forth with reference to FIGS. 3-5 and 7, above, in accordance with additional aspects of the invention. System 800 is similar to system 500 and, as with FIG. 5 with respect to FIG. 4, in FIG. 8, for convenience, the latter two digits of each numbered aspect in FIG. 8 are the same as those of similar aspects set forth above, in reference to FIG. 5. A cutaway 891 shows an inner water outlet 893, serviced by pipe 805, and its concentrically-held variably descending/ascending rounded-tipped spray modification piece 895. Spray modification piece 895 preferably comprises an axially expanding/contracting stem 897, which, preferably, is user adjustable, and, even more preferably, adjusts to be at a maximum flow rate when a selected temperature by the user matches the delivered temperature of the water being served. However, as the water temperature descends below the desired temperature, stem 897 contracts, bringing modification piece 895 upward, and tighter against inner water outlet 893. The net result of this activity is that, as the delivered water temperature indicates that the system 800 cannot meet the demand for hot water, specialized shower head 801 reduces the amount of water emitted, to give the system an opportunity to heat more water and deliver it—i.e., "catch up" with the demand from the user.

Figure 11:
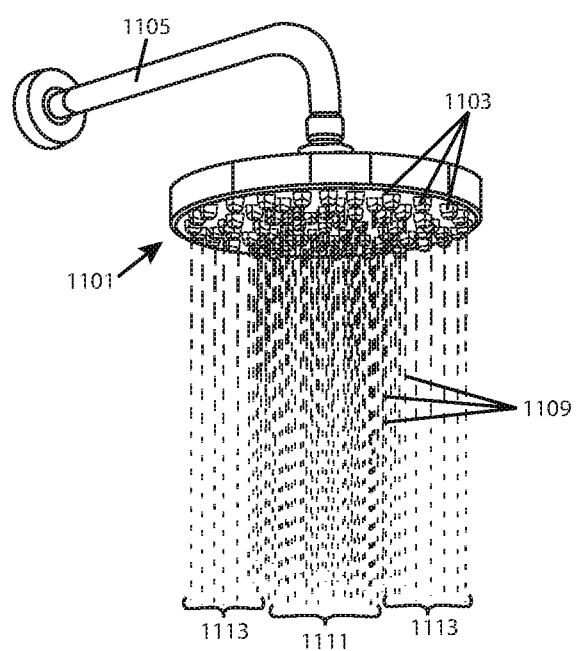
FIG. 11 depicts an exemplary shower head 1101 under lower than optimal pressure, as discussed in greater detail above, with reference to FIG. 8.

At this point, we will turn briefly to FIG. 11, to explain further aspects of the exemplary shower head 801 and system 800. As water pressure descends, typically, water emitted from a shower head, such as that pictured as 1101, tends to pool and become more concentrated in a central region 1111, as opposed to outer regions of the shower head plane 1113. As a result, the descending water streams/droplets 1109 tend to be of a far narrower breadth than when the shower head is under heavier pressure.

As shower head 801 begins emitting a lower pressure, due to reduced hot water availability, it combats this effect with new improvements. Owing to its rounded profile and interface, spray modification piece 895 creates an increasingly outward spray, the tighter it is pulled against the inner outlet 893. This, by itself, serves to increase the flow at the outside edge of the shower head. In addition, however, trenches or walls, such as the example shown as 899, which are preferably rounded on their inner side, and flat or barbed on their outer side, serve to aid in retaining the water at those outer reaches of the shower head.

Figure 9:
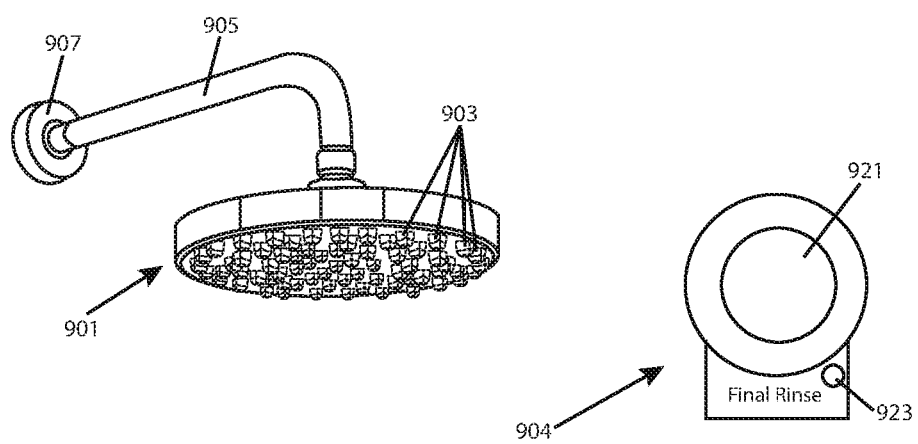
FIG. 9 depicts an exemplary GUI for a user of a system in accordance with aspects of the present invention, comprising a "final rinse" control.
Figure 10:
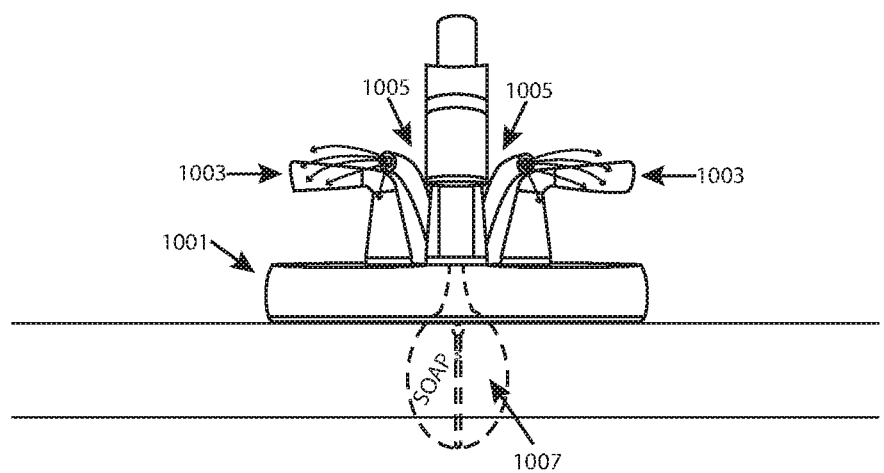
FIG. 10 depicts another form of GUI associated with a water service faucet 1001, using conventional user behavior, to perform a cleaning and/or antiseptic aspects of the present invention, relative to a fixture control.

FIG. 9 depicts an exemplary GUI 904 for a user of a system in accordance with aspects of the present invention, comprising a "final rinse" control. To assist a hot water deployment and management system, such as that discussed with reference to FIG. 5, above, a user may indicate when he or she is nearly done showering, which time to the end of showering may be adjusted by the user and/or system's experience. A user may depress such an indicator button 921, and an indicator light 923 may confirm to the user that he or she has indicated a "Final Rinse" time is beginning. The system then continues to deliver hot water until the user is finished, and may record the time it took the user to rinse. That time may then be used by the system to optimize the lead time for replacing outgoing hot water, from a service line, with cold water, obviating the need to pull back hot water into the tank to avoid heat loss through pipes in the walls—which other approaches were discussed in greater detail, above. To so replace outgoing hot water with cold, a switch may be actuated by the system at the hot water tank FIG. 10 depicts another form of GUI associated with a water service faucet 1001 using conventional user behavior, to perform a cleaning and/or antiseptic aspects of the present invention, relative to a fixture control. As a user washes his or her hands, face or other things in a sink he or she will naturally first handle the faucet handles, such as those shown as 1003. To aid in sanitizing the handles 1003, antiseptic, soap and/or rinsing spray nozzles or spigots 1005 may flow from and cover the touched surfaces of handles 1003 a short time before, during, and/or upon completion of use of the faucet and/or sink or bathroom area. The source of such antiseptic, soap and/or rinse may be a reservoir 1007, that may, in some embodiments, also service a separate soap and/or antiseptic delivery tool. In other embodiments, the reservoir (or a separate, additional reservoir) may be pressurized by some water pressure releasing into it, which pressurization may occur upon a user turning on the faucet handles (via a water inlet valve attached to and actuated by the faucet handles). In that embodiment, when the faucet handles are turned off, the valve releases pressure from the reservoir(s), and channels the flow out of the spigots and over the handled surfaces, cleansing them. In an alternative embodiment, pores on the surface of handles 1003 exude such antiseptic, soap and/or rinsing, rather than spraying it—either by osmotic, wicking forces or pumped delivery, which may be similarly timed. In one embodiment, a control system comprising such pumps servicing such pores also comprises sensors configured to detect when handles 1003 have been shut off by a user and triggers the pumps to exude an antiseptic fluid through the pores or rinsing spray nozzles after that time (optionally, after a delay.) Alternatively, to aid in effectuating the desired timing, a plumbing conduit, such as a valved channel that opens with the rotation of the handles 1003, may drive the actuation of nozzles 1005 at a point just before the off position of the faucet handles, leading to a brief spray or exuding of the antiseptic, soap and/or rinsing onto the handles.

Any of the embodiments discussed above may be applied in a wide variety of additional contexts, such as elevator GUI buttons and everyday door handles.

FIG. 11 depicts an exemplary shower head 1101 under lower than optimal pressure, as discussed in greater detail above, with reference to FIG. 8.

Figure 12:
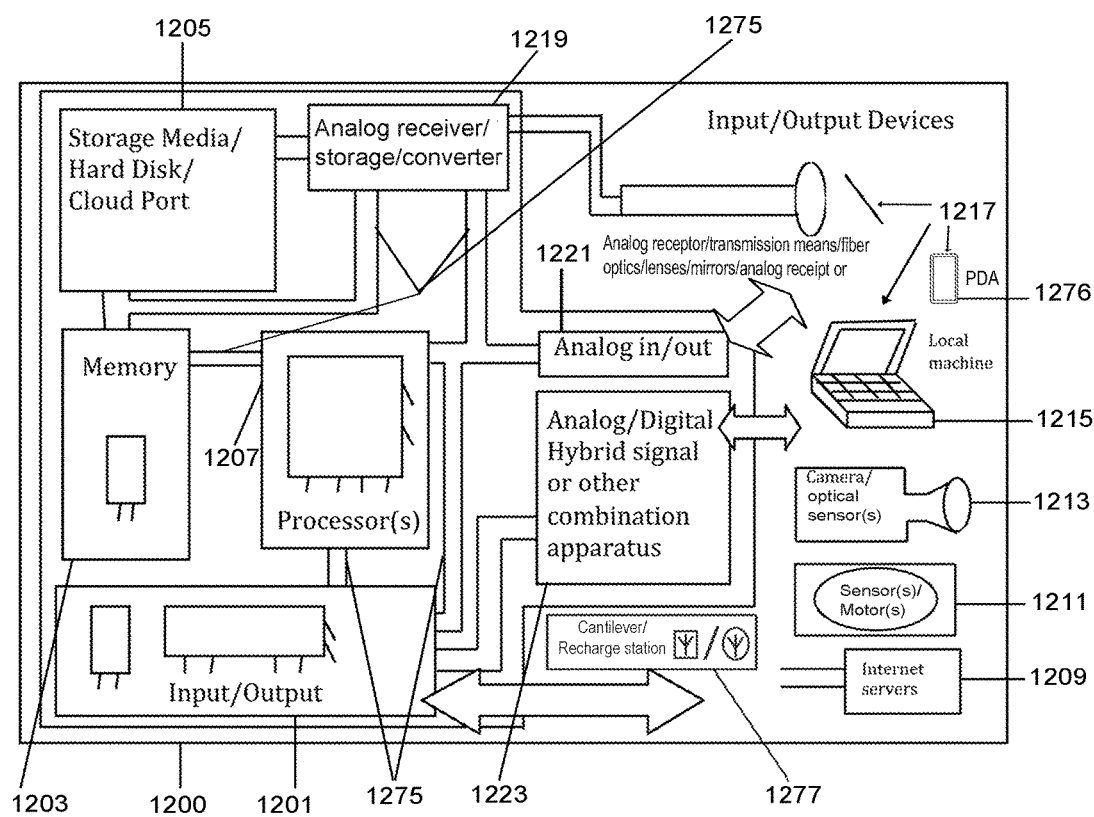
FIG. 12 is a schematic block diagram of some elements of an exemplary control system that may be used in accordance with aspects of the present invention.

FIG. 12 is a schematic block diagram of some elements of an exemplary control system 1200 that may be used in accordance with aspects of the present invention, such as, but not limited to, actuating sensors, pumps, motors, water and waste heat recapturing systems, and other actuators in connection with system functions, and for receiving, and taking actions based on user commands or other behavior, such as control sterilization actions. The generic and other components and aspects described herein are not exhaustive of the many different systems and variations, including a number of possible hardware aspects and machine-readable media that might be used, in accordance with the present invention. Rather, the system 1200 is described to make clear how aspects may be implemented. Among other components, the system 1200 includes an input/output device 1201, a memory device 1203, storage media and/or hard disk recorder and/or cloud storage port or connection device 1205, and a processor or processors 1207. The processor(s) 1207 is (are) capable of receiving, interpreting, processing and manipulating signals and executing instructions for further processing and for output, pre-output or storage in and outside of the system. The processor(s) 1207 may be general or multipurpose, single- or multi-threaded, and may have a single core or several processor cores, including, but not limited to, microprocessors. Among other things, the processor(s) 1207 is/are capable of processing signals and instructions for the input/output device 1201, analog receiver/storage/converter device 1219, analog in/out device 1221, and/or analog/digital or other combination apparatus 1223 to cause a display, light-affecting apparatus and/or other user interface with active physical controls, such as a "Final Rinse" indicating control and/or hot water usage settings (as may be comprised or partially comprised in a GUI) to be provided for use by a user on hardware, such as a personal computer monitor or PDA (Personal Digital Assistant) screen (including, but not limited to, monitors or touch- and gesture-actuable displays) or terminal monitor with a mouse and keyboard or other input hardware and presentation and input software (as in a software application GUI), and/or other physical controls. Alternatively, or in addition, the system, using processors 1207 and input/output devices 1219, 1221 and/or 1223, may accept and exert passive and other physical (e.g., tactile) user and environmental input and output.

For example, and in connection with aspects of the invention discussed in reference to the remaining figures, the system may carry out any aspects of the present invention as necessary with associated hardware and using specialized software, including, but not limited to, controlling the flow and recapture of hot water, reversing of variable-direction heat shielding pipes, activating specialized flash heating elements and deploying sanitizing sweats, sprays and other devices. The system may also, among many other things described for control systems in this application, respond to user, sensor and other input (for example, by a user-actuated GUI controlled by computer hardware and software or by another physical control) to activate/deactivate specialized water and heat saving systems, end-of-use and/or beginning-of-use actions (such as Final Rinse and other functions). The system 1201 may also permit the user and/or system-variation of settings for any of those aspects, including but not limited to the affects of user activity on modes of operation of the system, and send external alerts and other communications (for example, to users and administrators) via external communication devices, for any control system aspect that may require or benefit from such external or system-extending communications.

The processor 1207 is capable of processing instructions stored in memory devices 1203 and/or 1205 (and/or ROM or RAM), and may communicate with any of these, and/or any other connected component, via system buses 1275. Input/output device 1201 is capable of input/output operations for the system, and may include/communicate with any number of input and/or output hardware, such as a computer mouse, keyboard, entry pad, actuable display, networked or connected second computer, other GUI aspects, camera(s) or scanner(s), sensor(s), sensor/motor(s), range-finders, GPS systems, receiever(s), transmitter(s), transceiver(s), transflecting transceivers ("transflecters"), antennas, electromagnetic actuator(s), mixing board, reel-to-reel tape recorder, external hard disk recorder (solid state or rotary), additional hardware controls (such as, but not limited to, buttons and switches, and actuators, current or potential applying contacts and other transfer elements, light sources, speakers, additional video and/or sound editing system or gear, filters, computer display screen or touch screen. It is to be understood that the input and output of the system may be in any useable form, including, but not limited to, signals, data, commands/instructions and output for presentation and manipulation by a user in a GUI. Such a GUI hardware unit and other input/output devices could implement a user interface created by machine-readable means, such as software, permitting the user to carry out any of the user settings, commands and input/output discussed above, and elsewhere in this application.

1201, 1203, 1205, 1207, 1219, 1221 and 1223 are connected and able to communicate communications, transmissions and instructions via system busses 1275. Storage media and/or hard disk recorder and/or cloud storage port or connection device 1205 is capable of providing mass storage for the system, and may be a computer-readable medium, may be a connected mass storage device (e.g., flash drive or other drive connected to a U.S.B. port or Wi-Fi) may use back-end (with or without middle-ware) or cloud storage over a network (e.g., the internet) as either a memory backup for an internal mass storage device or as a primary memory storage means, or may simply be an internal mass storage device, such as a computer hard drive or optical drive.

Generally speaking, the system may be implemented as a client/server arrangement, where features of the invention are performed on a remote server, networked to the client and made a client and server by software on both the client computer and server computer. Input and output devices may deliver their input and receive output by any known means of communicating and/or transmitting communications, signals, commands and/or data input/output, including, but not limited to, input through the devices illustrated in examples shown as 1217, such as 1209, 1211, 1213, 1215, and 1277 and any other devices, hardware or other input/output generating and receiving aspects. Any phenomenon that may be sensed may be managed, manipulated and distributed and may be taken or converted as input or output through any sensor or carrier known in the art. In addition, directly carried elements (for example a light stream taken by fiber optics from a view of a scene) may be directly managed, manipulated and distributed in whole or in part to enhance output. It is to be understood that the system may use any form of electromagnetism, compression wave, heat or other phenomena that may be sensed, and may include directional and 3D locational information, which may also be made possible by multiple locations of sensing, preferably, in a similar, if not identical, time frame. The system may condition, select all or part of, alter and/or generate composite data from all or part of such direct or analog image or other sensory transmissions, including physical samples (such as DNA, fingerprints, iris, and other biometric samples or scans) and may combine them with other forms of data, such as image files, dossiers or metadata, if such direct or data encoded sources are used.

While the illustrated system example 1200 may be helpful to understand the implementation of aspects of the invention, it is understood that any form of computer system may be used to implement many control system and other aspects of the invention—for example, a simpler computer system containing just a processor (datapath and control) for executing instructions from a memory or transmission source. The aspects or features set forth may be implemented with, and in any combination of, digital electronic circuitry, hardware, software, firmware, or in analog or direct (such as electromagnetic wave-based, physical wave-based or analog electronic, magnetic or direct transmission, without translation and the attendant degradation, of the medium) systems or circuitry or associational storage and transmission, any of which may be aided with enhancing media from external hardware and software, optionally, by wired or wireless networked connection, such as by LAN, WAN or the many connections forming the internet or local networks. The system can be embodied in a tangibly-stored computer program, as by a machine-readable medium and propagated signal, for execution by a programmable processor. The method steps of the embodiments of the present invention also may be performed by such a programmable processor, executing a program of instructions, operating on input and output, and generating output. A computer program includes instructions for a computer to carry out a particular activity to bring about a particular result, and may be written in any programming language, including compiled and uncompiled, interpreted languages, assembly languages and machine language, and can be deployed in any form, including a complete program, module, component, subroutine, or other suitable routine for a computer program.

The embodiments and aspects of the invention set forth above are exemplary, and many variations and groupings, which are virtually unlimited, still fall within the scope of the invention. For example, additional waste heat reclamation technology, such as convective coupling of waste water pipes, or efferent and return pipes, may be used, and a system may use behavioral recognition and timing to optimize a hybridization of the heating pipes and insulating pipes set forth in FIGS. 6 and 7, and a boiler system with them, to optimize hot water delivery. In other embodiments, a system may use sensors, calendars and time-of-day of use to memorize, model or guess a user's schedule and future schedule, or an approximation thereof, to trigger any of the actions taken, as described in this application—such as, but not limited to, initiating the return of hot water to a service pipe after retraction, for use. In other aspects, a user's biometrics may be used to further optimize the system for a given user, and a user's present condition, through common use sensors. For example, infra-red motion detectors may track both the user's behavior and usage patterns, and bodily and ambient condition (e.g., ambient coldness, and amount of heat flux and loss from the user's body relative to the environment) to determine an amount of hot water, or current, or hot water flux and bodily heating resulting therefrom, to establish comfort for a user at a given moment entering or in a shower.

Figure 13:
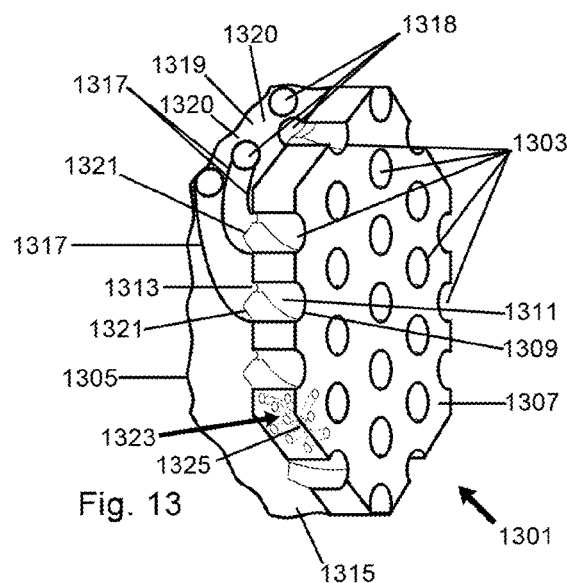
FIG. 13 is a perspective drawing of a fungible section of a continually sterilizing antiseptic surface.

FIG. 13 is a perspective drawing of an exemplary fungible section 1301 of a continually sterilizing antiseptic surface, in accordance with aspects of the present invention. As will be explained in greater detail below, in reference to FIG. 14, section 1301 may be placed in a surface-covering array, with several other, similar surface sections, to cover an area of any object that may be handled by a user, thereby creating a self-cleaning, antiseptic surface. Among other aspects, section 1301 may comprise a plurality of specialized ports, such as the examples pictured as 1303, for exuding water or other antiseptic fluids. When section 1301, and/or a surface comprising a number of such sections (such as exemplary surface 1401) discussed below, is placed over the surface of a object to provide an antiseptic barrier, one side—namely, side 1305—faces and covers the surface of the object while another side—namely, side 1307—faces outward, providing a new, antiseptic surface for the covered object.

Once in place over an object, section 1301 provides a new, protective surface over the object. And section 1301 may comprise a element, compound or other composition, structure and agent with anti-microbial properties (e.g., silver, gold, copper, catalytic agents, other anti-microbial agents, coating or doping). However, the antiseptic properties of section 1301 exceed those of such known, antimicrobial surfaces, due to several additional aspects. First, as shown in a cross-section at exemplary port 1309 (which is partially encompassed by section 1301, at its border), each port 1303 comprises a ramped inner channel 1311, which narrows to a smaller, interior inlet 1313, facing side 1305. Also on side 1305, abutting each such smaller, interior inlet 1313 of each port, is an absorbent, water-passing sponge material layer 1315. Layer 1315 generally absorbs any fluid poured onto it, and expresses that fluid if compressed, and may be made of any number of traditional sponge materials. However, in addition, layer 1315 comprises fluid-guiding channel walls, such as the examples pictured as channel walls 1317. Channel walls 1317 are composed of a liquid-proof or liquid-resistant material (such as certain plastics, resins, rubber and polymers) and resist the diffusion of fluids across them more greatly than the other, surrounding sponge materials of layer 1315. Channel walls 1317 serve to guide antiseptic fluids moving through layer 1315 (e.g., via gravity, diffusion and compression) toward each port 1303 on the object-facing side 1305. Each channel thus terminates at a port. In addition, each channel begins at a separate, dedicated entrance 1318 (or approximately so) at an upward-facing edge 1319 of section 1301. In this way, as fluids are poured into the top edge 1319 of section 1301, an approximately equal amount of that fluid is channeled downward and to the right (in the perspective of the figure) to each port 1303. Some open areas 1320 of the leading edge 1319, and throughout the layer 1315, however, permit the straight downward passage of antiseptic fluids, which can exit through the bottom of section 1301 (in the perspective of the figure), and into a neighboring section (when placed in a surface-covering array, as discussed in greater detail in FIG. 14, below.) The proportion of open areas 1320 to channels 1317 within a section such as 1301 will depend on the positioning of the section in an array, to achieve a uniform distribution of fluid supplied to each port of each section in such an array. The diffusion and gravitational pressure of such fluids against the object-facing side of each port within a channel 1317 is generally not sufficient to cause the fluid to completely pass through the ramped inner channels 1311 and exit ports 1303 at side 1307. However, when side 1307 is pressed, its rigid panel structure, and free edges permit it to move toward side 1305, compressing layer 1315 further, and increasing the compression pressure of any fluids held within it. Compression spikes 1321 may be included at the base of each port and abutting layer 1315, aiding in guiding and intensify that compression pressure toward inlet 1313. With that added pressure, from a person pushing against or otherwise handling side 1307, the fluids will begin to enter the inlet, until they emerge at the top of ramped channel 1311. At that point, the fluid(s) begin a steady descent, with gravity, exiting the ramped inner channel 1311 at side 1307 of the port 1309, in a stream over time (after a person has handled the surface). By selecting an antiseptic fluid of a particular viscosity, and with other particular reactions to stress, as well as by modifying the size and slope of channel 1311, a precise length of time can be selected for the antiseptic fluid to flow out of each port 1303, and cover the outer surface of side 1307, thereby washing and disinfecting it. Preferably, and especially when using disinfecting fluids (such as water) requiring the time to penetrate bacterial cell walls, the length of time that the fluid flows over or stands on the surface of side 1307 exceeds 5 seconds. However, with other, more rapidly acting disinfecting fluids, such as those incorporating chlorine, the flow and stand time prior to evaporation, can be far shorter. In the case of exceptionally small pore sizes (as in the nanometer range) a meniscus-breaking nib may be included at the lower, outer edge of port 1303, to aid in encouraging emerging droplets to flow out of the port during this process. The amount of fluid flowing out of the pores 1303 increases with the pressure and amount of surface 1307 handling by a user, in a tapering, but proportionate function. As a user presses against side 1307, there would be some risk of backflow within inner channels 1311 of each port 1303, especially if the user's skin creates a seal with the edge of a port. To combat that tendency, an inner matrix of smaller tubules 1323 allows the surface of side 1307 to breathe with a plethora of distributed openings about the outer surface and within ports 1303. The matrix of tubules, sharing common passages 1325, prevent such seals from occurring by allowing air within each port 1303 to escape laterally into the matrix. To avoid antiseptic fluids from escaping into the matrix, the size of the smaller tubules may be made small enough to prevent larger compounds of the fluid to escape, while permitting smaller air molecules to enter. Alternatively, any entrance to the matrix within each port can reside on an upper surface, where the fluid does not flow as greatly.

Ports 1303 preferably cover the surface of side 1307, but may be periodically or randomly set at intervals away from one another, as pictured. Preferably, the spacing is not so great that, given the droplet formation and other colligative properties of the antiseptic fluid used, the fluid flow would miss any region of side 1307 during and after outflow from the ports 1303.

Figure 14:
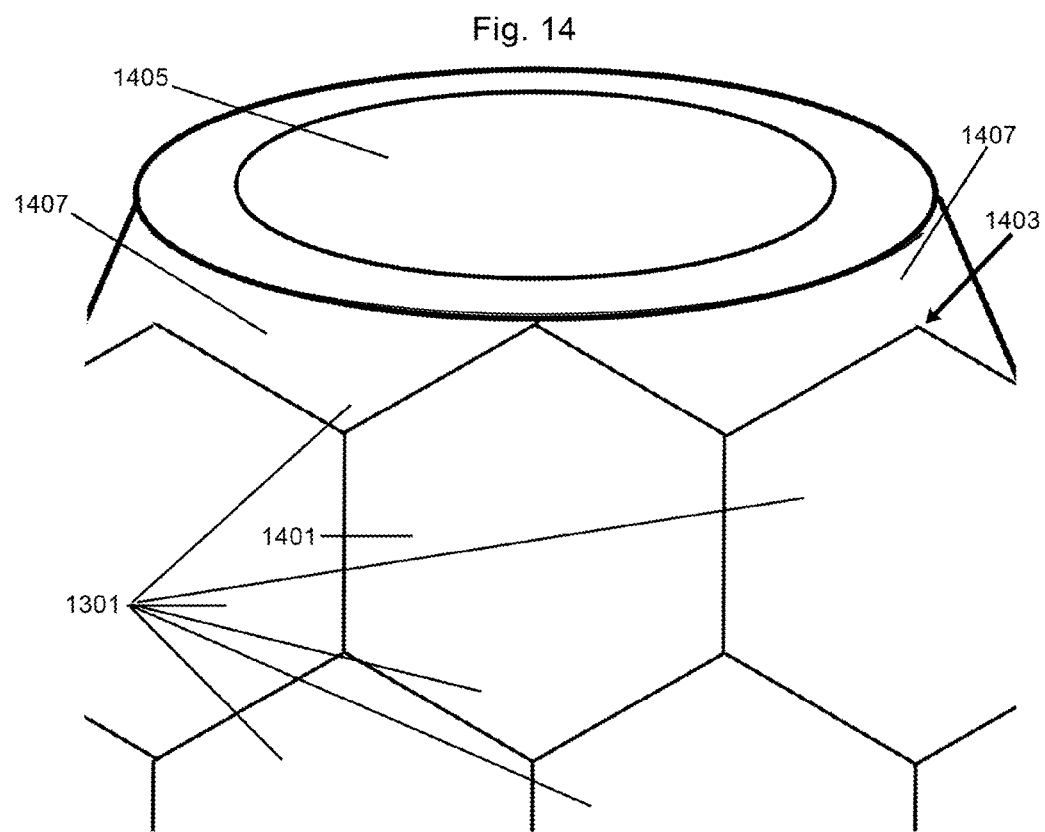
FIG. 14 is a front view of an exemplary surface composed of fungible sections of continually sterilizing antiseptic sections, such as the exemplary section set forth in FIG. 13, above.

FIG. 14 is a front view of an exemplary surface 1401 composed of an array 1403 of fungible sections 1301, such as the exemplary section set forth in FIG. 13, above. As discussed in FIG. 13, antiseptic fluids can pass through the spongy layer of the object-facing sides of each section, and through to one another, in an approximately even distribution covering an outer surface 1401 created by the array. To supply each of those sections, an upper filling port 1405 is provided. An administrator maintaining array 1403 may supply each port (not pictured) of each section by filling a reservoir 1407 underneath filling port 1405. Reservoir 1407 may itself comprise a spongy material, or an open vessel and, optionally, may be enclosed by a user with a lid (not pictured). To allow the flow of antiseptic fluid to each section, straight passages, as discussed in FIG. 13, above, may be provided at the base of reservoir 1407. Optionally, channels may be provided within reservoir 1407 to uniformly distribute the fluid to the channel entrances at the top edge 1319 of each section, as discussed above in reference to FIG. 13.

As with the antiseptic devices set forth with reference to FIG. 10, above, the surface devices set forth in reference to FIGS. 13 and 14 may optionally be controlled by a control system, such as the control system set forth in FIG. 12, above, instead or in addition to the structural techniques set forth in FIGS. 13 and 14. More specifically, such a control system may comprise sensors, such as the examples pictured as 1327, and pumps, such as the example pictured as 1329, configured to move antiseptic fluid out of pores 1303, covering the outer surfaces covering objects, as set forth above, upon detecting the manual touching of surface 1307 and 1401 (optionally, after a time delay measured by the control system.)

Any of the embodiments discussed above may be applied in a wide variety of contexts, such as elevator GUI buttons and everyday door handles.

I claim:

1. An antiseptic device comprising:
   an outer surface on a first side of said device, wherein said outer surface comprises at least one port connected with antiseptic hardware;
   wherein said antiseptic hardware comprises a reservoir and at least one movable panel, configured to move toward a second, inward-facing side of said device in reaction to pressure against said outer surface of said device; and
   wherein said antiseptic hardware comprises at least one channel, different from said at least one port, wherein said at least one channel comprises liquid-proof or liquid-resistant fluid-guiding walls comprising curved angles different from angles of walls of any of said at least one port and configured to guide an antiseptic fluid to each of said at least one port and from said reservoir.

2. The antiseptic device of claim 1, comprising a filling port at or about the top of said antiseptic device.

3. The antiseptic device of claim 1, wherein said reservoir comprises a spongy material configured to absorb, distribute and exude said antiseptic fluid.

4. The antiseptic device of claim 3, wherein said spongy material is configured to exude said antiseptic fluid through said at least one port when compressed.

5. The antiseptic device of claim 4, wherein said spongy material abuts and is attached to said movable panel, and is configured to be compressed by said movable panel when said outer contact surface is touched by a user.

6. The antiseptic device of claim 5, wherein said spongy material abuts said at least one channel configured to guide an antiseptic fluid to each of said at least one port.

7. The antiseptic device of claim 6, wherein said at least one port comprise at least part of a plurality of sloped interior channels.

8. The antiseptic device of claim 7, wherein said at least one sloped interior channel are partially comprised in and/or at least partially abutting the bottom of the interior of at least one of said at least one port.

9. A self-cleaning user interface device, comprising:
- a user-actuable moving part, wherein said user-actuable moving part is configured for placement in at least an on position and an off position;
- a reservoir connected with said user-actuable moving part;
- at least one port positioned above a handled surface of said user-actuable moving part; and
- a control system comprising sensors configured to sense when said user-actuable moving part is placed in said on position or said off position;
- wherein said control system is configured to release water or other antiseptic fluid, covering said handled surface, upon said sensors sensing that said user-actuatable moving part has been placed in said off position.

10. The self-cleaning user interface device of claim 9, wherein said user-actuable moving part is configured to load and pressurize said reservoir, and wherein said reservoir is configured to hold water or another antiseptic fluid when placed in said on position.

11. The self-cleaning user interface device of claim 9, wherein said user-actuable moving part is configured to release water or other antiseptic fluid, covering said handled surface, upon being placed in said off position, after a delay.

12. The self-cleaning user interface device of claim 9, wherein said control system comprises pumps configured to pump antiseptic fluid out of said at least one port.

13. A method for providing an antiseptic surface for an object, comprising the following steps:
- attaching an antiseptic device to said object, wherein said device comprises an outer surface on a first side of said device, wherein said outer surface comprises at least one port connected with antiseptic hardware;
- wherein said antiseptic hardware comprises a reservoir and at least one movable panel, configured to move toward a second, inward-facing side of said device in reaction to pressure against said contact surface of said device; and
- wherein said antiseptic hardware comprises at least one channel, different from said at least one port, wherein said at least one channel comprises liquid-proof or liquid-resistant fluid-guiding walls comprising curved angles different from angles of walls of any of said at least one port and configured to guide an antiseptic fluid to each of said at least one port and from said reservoir.

14. The method for providing an antiseptic surface for an object of claim 13, comprising the following additional step:
- touching said outer contact surface and moving said movable panel, causing said antiseptic fluid to escape from said at least one port and cover said outer contact surface.

15. The method for providing an antiseptic surface for an object of claim 13, comprising the following additional step:
- refilling said reservoir with said antiseptic fluid.

* * * * *